(12) United States Patent
Weidmann et al.

(10) Patent No.: US 10,101,207 B2
(45) Date of Patent: Oct. 16, 2018

(54) VAPOUR PHASE SPECTROSCOPY

(71) Applicant: ITI Scotland—Scottish Enterprise, Glasgow (GB)

(72) Inventors: Damien Weidmann, Reading (GB); Neil Angus Macleod, Oxford (GB)

(73) Assignee: ITI SCOTLAND—SCOTTISH ENTERPRISE, Glasgow (GB)

( * ) Notice: Subject to any disclaimer, the term of this patent is extended or adjusted under 35 U.S.C. 154(b) by 0 days.

(21) Appl. No.: 14/726,388

(22) Filed: May 29, 2015

(65) Prior Publication Data
US 2015/0260574 A1 Sep. 17, 2015

Related U.S. Application Data

(63) Continuation of application No. PCT/GB2013/053160, filed on Nov. 29, 2013.

(51) Int. Cl.
*G01J 3/42* (2006.01)
*G01N 21/3504* (2014.01)
(Continued)

(52) U.S. Cl.
CPC .............. *G01J 3/42* (2013.01); *G01J 3/0205* (2013.01); *G01N 21/274* (2013.01); *G01N 21/3504* (2013.01); *G01N 1/405* (2013.01); *G01N 21/031* (2013.01); *G01N 21/0332* (2013.01); *G01N 21/05* (2013.01); *G01N 2001/4033* (2013.01);
(Continued)

(58) Field of Classification Search
CPC ............. G01N 21/274; G01N 21/3504; G01N 21/031; G01N 21/0332; G01N 21/05; G01J 3/42; G01J 3/0205
See application file for complete search history.

(56) References Cited

U.S. PATENT DOCUMENTS

2009/0101822 A1* 4/2009 Mitra ................. G01N 21/3151
250/339.1
2009/0173145 A1* 7/2009 Martin ................... G01N 21/78
73/61.41
(Continued)

FOREIGN PATENT DOCUMENTS

| JP | 2000180356 A | 6/2000 |
|---|---|---|
| JP | 2004-91917 A | 3/2004 |
| JP | 2005326273 A | 11/2005 |

OTHER PUBLICATIONS

Ruxton et al. "Concentration measurements of complex mixtures of broadband absorbers by widely tunable optical parametric oscillator laser spectroscopy", Proceedings of SPIE, vol. 8537, Nov. 8, 2012, p. 85370I XP055101890, ISSN: 0277-786X, DOI: 10.1117/12. 971184.*

(Continued)

*Primary Examiner* — Casey Bryant
(74) *Attorney, Agent, or Firm* — Perkins Coie LLP

(57) ABSTRACT

A method is provided of obtaining a vapor phase spectrum of a compound. The method comprises providing an isolated condensed phase sample of the compound, vaporizing the sample and supplying the vapor to an absorption cell of a spectrometer. A rate at which vapor enters the absorption cell is determined and a steady state concentration of vapor in the absorption cell is established. The spectrum of the vapor is then measured.

19 Claims, 17 Drawing Sheets

(51) Int. Cl.
*G01N 21/27* (2006.01)
*G01J 3/02* (2006.01)
G01N 21/03 (2006.01)
G01N 21/05 (2006.01)
G01N 1/40 (2006.01)
G01N 21/35 (2014.01)
G01N 21/15 (2006.01)

(52) U.S. Cl.
CPC .................. *G01N 2021/158* (2013.01); *G01N 2021/3595* (2013.01)

(56) References Cited

U.S. PATENT DOCUMENTS

2013/0238252 A1* 9/2013 Perenon .............. H01J 49/0018
702/23
2016/0124112 A1* 5/2016 Daito ....................... G01V 8/12
356/436

OTHER PUBLICATIONS

Sharpe et al. "Gas-Phase Databases for Quantitative Infrared Spectroscopy", Applied Spectroscopy 58 (12), published 2004, pp. 1452-1461.*
Office Action dated Oct. 10, 2017 for Japanese Application No. 2015-544536 of Weidmann, D. et al., filed Nov. 29, 2013.
Ruxton K., et al., "Concentration Measurements of Complex Mixtures of Broadband Absorbers by Widely Tunable Optical Parametric Oscillator Laser Spectroscopy", Proc. of SPIE, vol. 8537, Nov. 8, 2012, pp. 853701-1-853701-12.

* cited by examiner

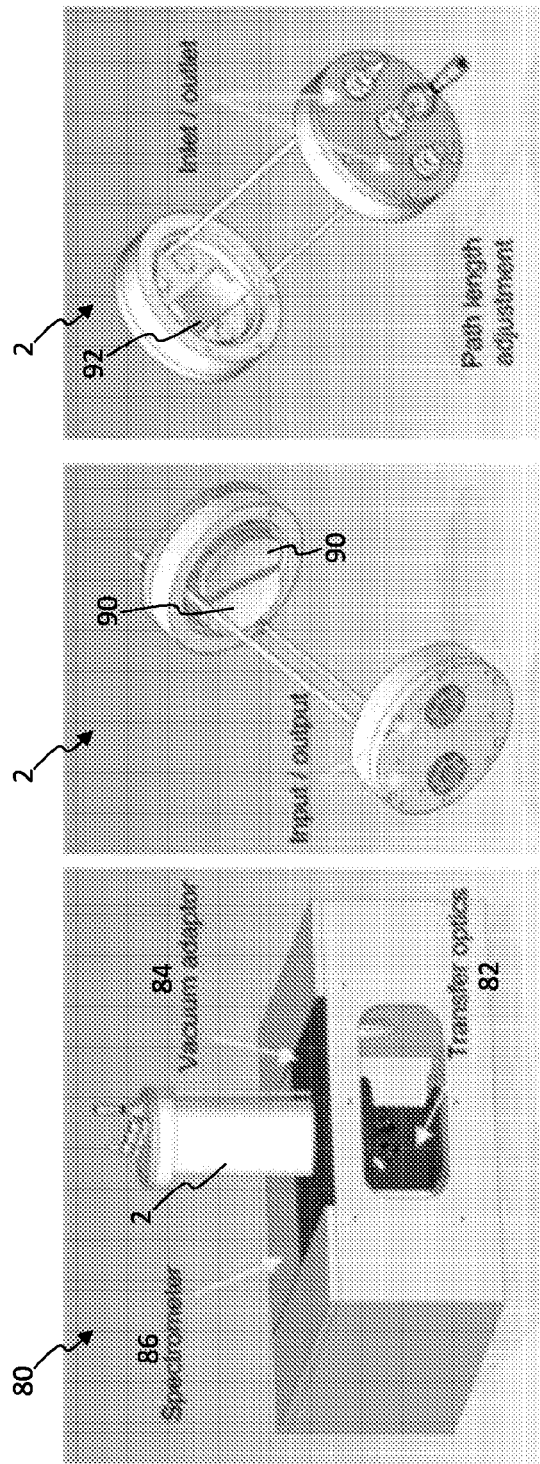

VAPOUR PHASE SPECTROSCOPY

This application is a continuation of International Application No. PCT/GB2013/053160, filed Nov. 29, 2013; which claims priority to Great Britain Patent Application No. 1221678.4, filed Nov. 30, 2012. The contents of the above-identified applications are incorporated herein by reference in their entireties.

FIELD OF INVENTION

The present invention relates to spectroscopy of volatile compounds, in particular to obtaining high quality pure vapour phase spectra. The invention is suitable for providing high quality, quantitative reference spectra for in situ and remote detection of volatile compounds.

BACKGROUND OF INVENTION

A known technique for obtaining vapour phase spectra involves heating up a solid sample of a compound, estimating the concentration of the resulting vapour using the Clausius-Clapeyron relation, and measuring the spectrum of the vapour. This results in a measured spectrum for a given vapour concentration.

A known way to implement this approach is to coat an inert base such as small silica beads with a layer of the sample compound. The thin layer can then undergo a controlled vaporisation and its spectrum be measured. This method is suitable for unstable compounds which must be used in small quantities to prevent them from decomposing, potentially explosively, and therefore reduces the risks associated with heating up a solid sample of an unstable compound. However, the emission rate is very low with this technique, and for volatile compounds it is difficult to create a stable, thin condensed phase coating because the compound evaporates.

To reduce evaporation of volatile compounds and to desensitise unstable compounds, a sample can be mixed with a solvent to form a dilute solution. A combined vapour phase spectrum of the mixture is measured and the sample spectrum is extracted from the combined spectrum by post-analysis. However, a simple subtraction of the pure solvent spectrum is not sufficient because of complex molecular interactions between the dissolved sample compound and the solution, and post-analysis techniques do not adequately account for this. Furthermore, to measure the separate vapour concentrations of the sample compound and the vaporised solvent, gas chromatography mass spectrometry is used but this introduces inaccuracies.

To desensitise an unstable sample compound without using a solvent, the sample may be deactivated. However, this chemically changes the sample, which is likely to create differences in the spectrum that are difficult to predict or recognise.

Furthermore, the quantitative accuracy of any technique using the Clausius-Clapeyron relation is restricted because of condensation and adsorption effects which move the true vapour concentration away from the calculated value, and also because assumptions inherent in the Clausius-Clapeyron relation limit its accuracy.

Another known technique for obtaining pure vapour phase spectra is to extrapolate from condensed matter phase spectra. The extrapolation is not straightforward, however, because intermolecular interactions present only—or to a greater extent—in the condensed phase are difficult to predict with quantitative accuracy. Also, if the vapour phase is less stable and readily dissociates into decomposition compounds with their own absorption bands, this can be difficult to predict from condensed phase data alone.

The present invention aims to address one or more of the deficiencies associated with the prior art.

SUMMARY OF INVENTION

The invention resides in a method of obtaining a vapour phase spectrum of a compound. The method comprises the steps of providing an isolated condensed phase sample of the compound; vaporising the sample and supplying the vapour to an absorption cell of a spectrometer; determining a rate at which vapour enters the absorption cell; establishing a steady state concentration of vapour in the absorption cell; and measuring the spectrum of the vapour. This method enables high accuracy measurement of a pure vapour phase spectrum of an isolated, high purity sample of a compound.

The step of establishing a steady state concentration of vapour helps to increase accuracy by reducing the impact of condensation and other effects.

The invention may also be expressed as a corresponding apparatus for obtaining a vapour phase spectrum of a compound. The apparatus comprises a vaporising chamber for receiving an isolated condensed phase sample of the compound; a spectrometer including an absorption cell in fluid communication with the vaporising chamber; a monitoring means for monitoring the rate at which the compound in a vaporised form enters the absorption cell; and a flow means for maintaining a steady flow of gas through the absorption cell in order to establish a steady state concentration of the vaporised compound in the absorption cell ready for measurement of the vapour phase spectrum.

The spectrum of the compound is suitably an absorption spectrum.

Preferably, the providing step comprises isolating the condensed phase sample by recovering it from a solution. Solutions are readily available and easily transportable, especially for explosives which must be stored and transported according to a highly regulated legal framework that often requires sale and transportation of explosives only in the form of a solution.

In order to contribute to a high quantitative accuracy of the spectra, the isolated sample preferably has a purity of at least 99% by mass.

The method of the invention is particularly apt to be used with explosive compounds.

Permeation sources enable a controlled, usually constant, rate of permeation to be achieved. This contributes to high quantitative accuracy, and accordingly the vaporising step advantageously comprises vaporising the sample from a permeation source. In that case, the permeation source is preferably provided in an oven at a controlled temperature to enable a controlled vaporisation of the compound from the permeation source. This stabilises conditions and contributes towards achieving a very constant and well defined permeation rate.

The determining step preferably comprises measuring a rate of permeation from the permeation source. To achieve this, it is suitable to monitor mass loss from the permeation source, in which case mass loss is preferably monitored using a balance having an accuracy of at least 10 μg. This contributes to high accuracy of the overall method.

The determining step may comprise a pre-calibration step to pre-calibrate the permeation source. In that case, the pre-calibration step preferably comprises taking mass loss data in high stability conditions enabling measurement of a permeation rate to an accuracy of 1%.

Measuring the mass loss may be carried out during at least one of the establishing and measuring steps. Monitoring mass loss simultaneously in this way provides mass loss data for appropriate ambient conditions and also provides a time-efficient way of proceeding.

The establishing step preferably comprises maintaining a steady flow through the absorption cell.

This helps to establish a steady state vapour concentration which helps to minimise the impact of condensation and other effects. The steady state is advantageously established over a period of at least 24 hours. This helps to ensure that a true steady state is achieved. The steady state concentration of the vapour is suitably in the range 1 ppb to 3000 ppb. Low concentrations in this range produce reference spectra that advantageously enable detection of vapour phase compounds in low concentrations.

The method may further comprise monitoring the temperature in the absorption cell. This helps to determine accurately vapour concentration in the absorption cell.

Spectra in the infrared are suitable for various vapour detection applications.

The method may further comprise comparing a measured vapour phase spectrum of the sample compound with a condensed phase spectrum of the same compound to identify distinguishing features for specific identification of the compound in the vapour phase. The vapour phase spectrum may be used to calibrate an optical instrument for detecting the compound in the vapour phase.

The inventive concept also extends to an optical instrument calibrated according to the method of the invention.

BRIEF DESCRIPTION OF DRAWINGS

Specific embodiments of the invention will now be described, by way of example, with reference to the accompanying drawings, of which:

FIG. 7 is a perspective view of a multi-pass spectrometry absorption system suitable for measuring a vapour phase spectrum as part of the method of FIG. 2;

FIG. 8 is a perspective view of an absorption cell of the system of FIG. 7 with its outer body removed so that the internal optics are visible;

FIG. 9 is a further perspective view of the absorption cell of the system of FIG. 7 with its outer body removed so that the internal optics are visible;

Throughout the figures, like reference numerals are used to denote like features.

DETAILED DESCRIPTION OF SPECIFIC EMBODIMENTS

Figure 1:
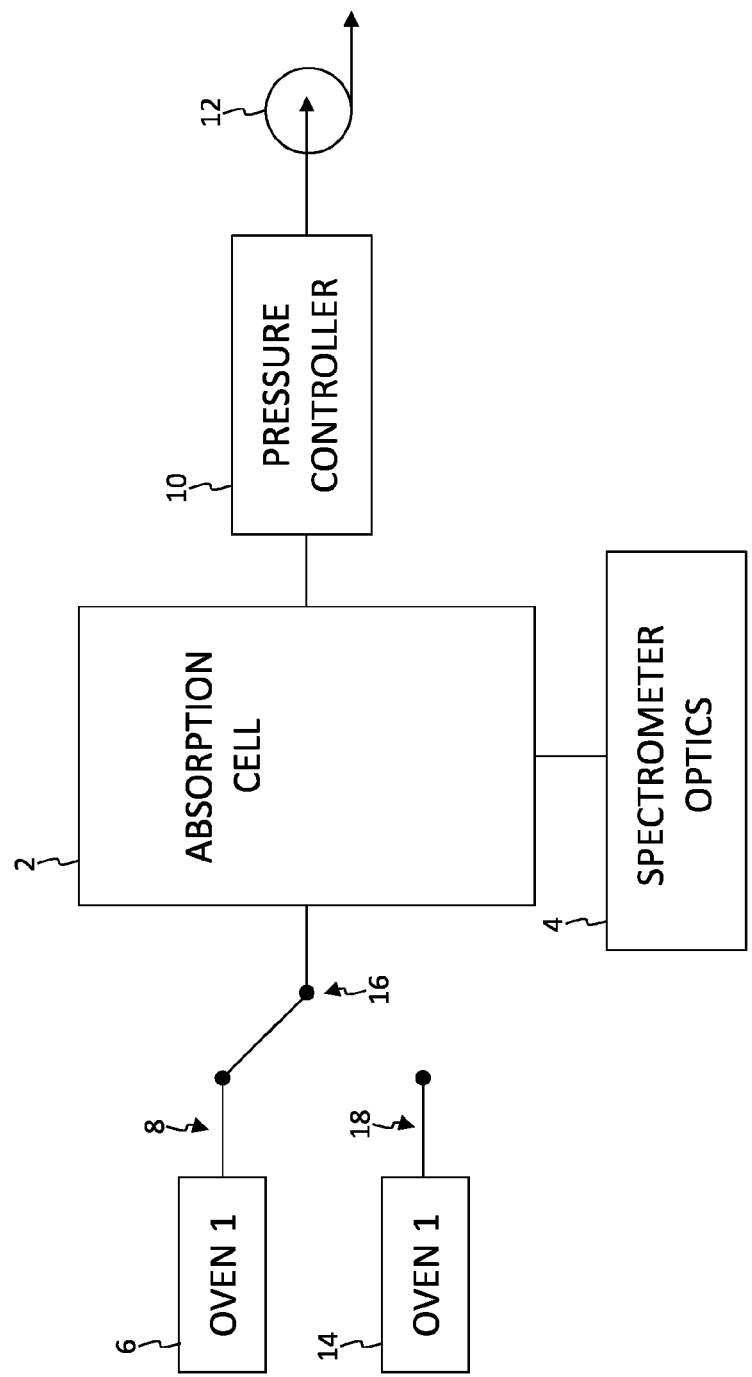
FIG. 1 is a schematic block diagram showing the arrangement of a spectrometer and other apparatus for performing a method according to an embodiment of the invention.

As shown in FIG. 1, apparatus suitable for carrying out a method according to an embodiment of the invention comprises a spectrometer including an absorption cell 2 coupled to spectrometer optics 4 for measuring the absorption spectrum of a sample compound provided within the absorption cell 2. An oven 6 is provided for heating a condensed phase sample of the compound so that the sample vaporises, thereby enabling a vapour phase spectrum to be measured.

The oven 6 is in communication with the absorption cell 2 via a gas line 8 to allow vapour produced in the oven 6 to flow to the absorption cell 2 to be measured. The oven 6 is located as close as practically possible to the absorption cell 2 in order to minimise the length of the gas line 8. A dry nitrogen gas line (not shown) with an inlet pressure of around 2.7 Bar is fed to the absorption cell 2 from pressurised cylinders for supplying nitrogen as a carrier gas. Nitrogen is spectrally inactive in the infrared and will not therefore interfere with measurement of the sample compound in the absorption cell 2.

The absorption cell 2 is also coupled to a pressure controller 10 and a pump 12 which draw gas across the absorption cell 2 in order to create a flow of vapour in the cell 2. Gas therefore flows along the gas line 8 and the nitrogen gas line, through the absorption cell 2, and out through the pressure controller 10 and the pump 12. Waste gases are vented out of the laboratory through an exhaust line (not shown).

The various gas lines are provided as flexible steel tubing with VCR® fittings providing the various connections. With a nitrogen cylinder volume of 50 liters at a typical pressure, the lifetime of a single cylinder is around 14 days with the pump 12 providing a maximum flow rate of around 500 ml/min.

Using this arrangement of apparatus, the absorption spectrum of vapour flowing through the absorption cell 2 can be measured using the spectrometer optics 4 coupled to the absorption cell 2.

This embodiment also includes the option of a second oven 14 whose gas line 18 may be connected to the absorption cell 2 using a switch 16 in order that the spectrometer may still be used while the other oven 6 is being cleaned or otherwise maintained. This is particularly useful since it takes at least 24 hours for a steady state vapour concentration in the absorption cell 2 to be reached.

Figure 2:
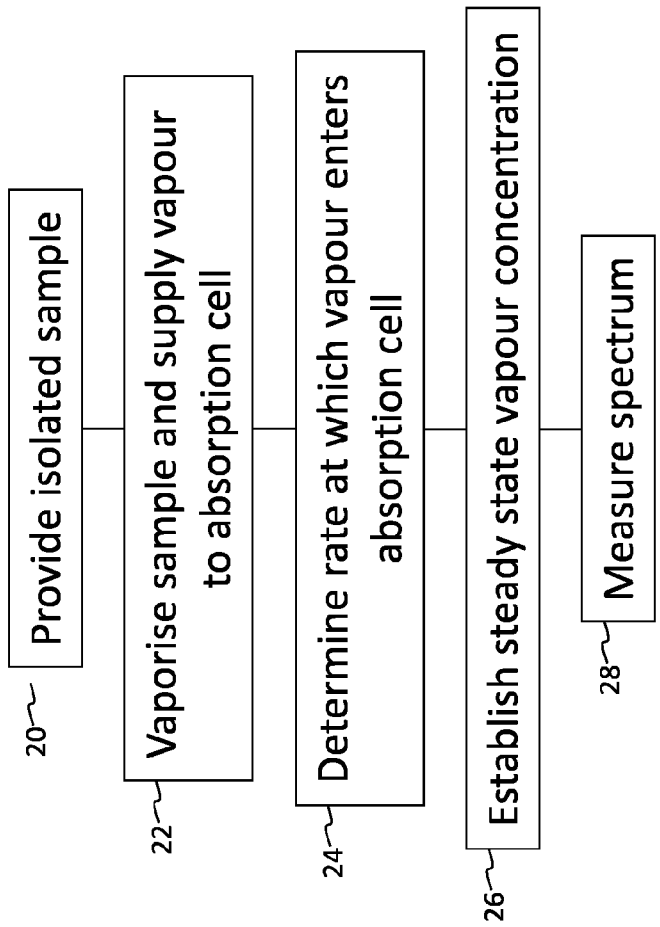
FIG. 2 is a flow chart showing the method mentioned in relation to FIG. 1.

The method of the present embodiment involves providing an isolated sample of the sample compound, as indicated at step 20 in FIG. 2. This sample is a compound whose vapour phase spectrum is to be measured, and a pure form of the compound is isolated to begin the process as will be described with reference to FIGS. 3 and 4. The isolated sample may be in solid or liquid form depending on the compound, but once isolated it is in the condensed phase ready for vaporisation. At step 22, the sample is vaporised and supplied to an absorption cell of a spectrometer, in order for its spectrum to be measured. The rate at which the vapour enters the absorption cell is determined at step 24. This opens the possibility of producing quantitative reference spectra of a range of sample compounds.

At step 26, a steady state vapour concentration is established. As a result, condensation effects within the apparatus may be ignored, thereby facilitating an accurate measurement of the vapour concentration in the absorption cell. Finally, at step 28 the spectrum of the vapour phase sample is measured. This provides a vapour phase absorption spectrum of a sample compound whose vapour concentration is known with improved accuracy.

The process of obtaining an isolated condensed matter phase sample of the compound under investigation will now be described with reference to FIGS. 3 and 4. Solutions of sample compounds in common solvents are readily available and a pure condensed phase sample can be isolated from solution using a rotary evaporator.

Figure 3:
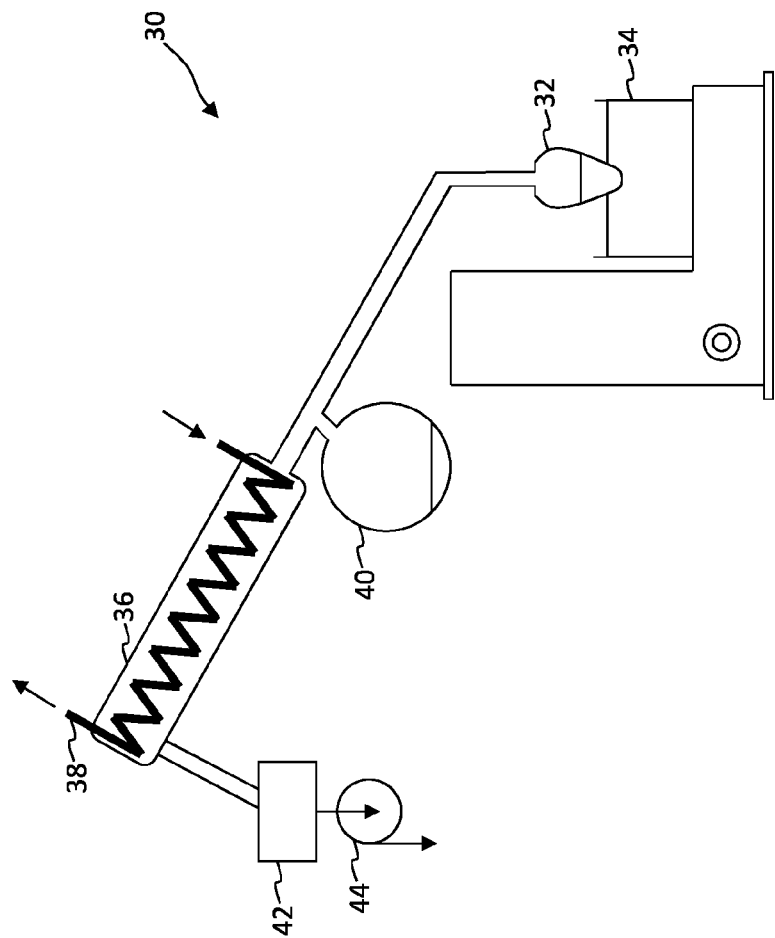
FIG. 3 is a schematic diagram of a rotary evaporator for isolating a sample as part of the method of FIG. 2.

As shown in FIG. 3, the rotary evaporator 30 comprises a small glass evaporation flask 32 for containing the sample in solution, a temperature-controlled water bath 34, a distillation tube 36 in communication with the evaporation flask 32 and provided with condensation tubing 38, and a large glass collection flask 40 for recovering the pure liquid solvent. A vacuum controller 42 and pump 44 are provided to create a partial vacuum in the distillation tube 36 to aid evaporation of the solvent. Cold water is caused to flow through the condensation tubing 38 in order to bring the temperature of the vapour in the distillation tube 36 down and induce condensation of the solvent in the distillation tube 36.

Figure 4:
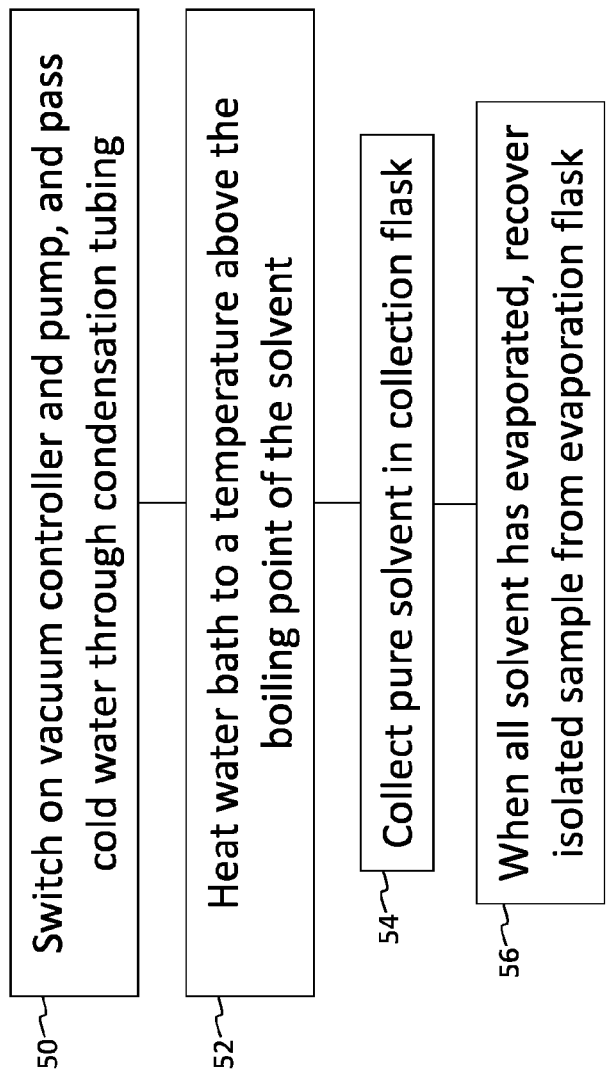
FIG. 4 is a flow chart showing a method of isolating a sample as part of the method of FIG. 2 and using the rotary evaporator of FIG. 3.

With reference to FIG. 4, the basic approach is to switch on the vacuum controller and pump, and to pass cold water through the condensation tubing, at step 50, followed by heating water in the water bath 34 to a temperature exceeding the boiling point of the solvent, at step 52, so that a vapour of the solvent fills the space defined by the evaporation flask 32, the distillation tube 36 and the collection flask 40. The condensed solvent is then collected at step 54 as a pure liquid in the collection flask 40 and when all the solvent has been collected, a pure condensed matter phase—either liquid or solid—sample of the compound is recovered at step 56 in the evaporation flask 32.

Once a pure sample has been recovered it can be vaporised as described with reference to FIG. 2 in order to measure its vapour phase spectrum. The step 22 of vaporising the sample including monitoring mass loss will now be described with reference to FIGS. 5 and 6.

Figure 5:
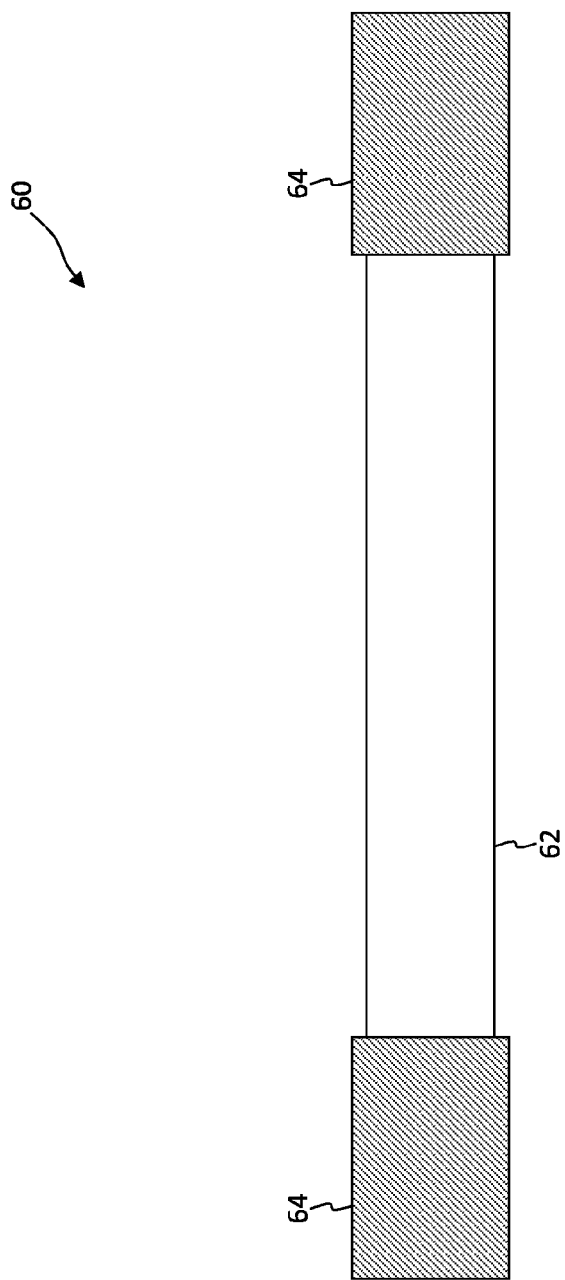
FIG. 5 is a cross-sectional diagram showing a typical permeation tube suitable for vaporising the sample as part of the method of FIG. 2.

For the vaporisation step 22, the sample is provided as a permeation source in the form of a permeation tube 60. Permeation tube technology enables a constant rate of vapour to permeate from inside the tube 60 to the outside, thereby enabling a highly controlled, quantitative vaporisation to be achieved. Referring to FIG. 5, the permeation tube 60 consists of a tube made from a partially permeable membrane 62, with end seals 64 on each end. A sample of condensed phase compound can be placed inside the permeation tube 60 and the interaction between the sample vapour and the membrane 62 determines the rate at which the vaporised compound permeates from the tube 60.

Figure 6:
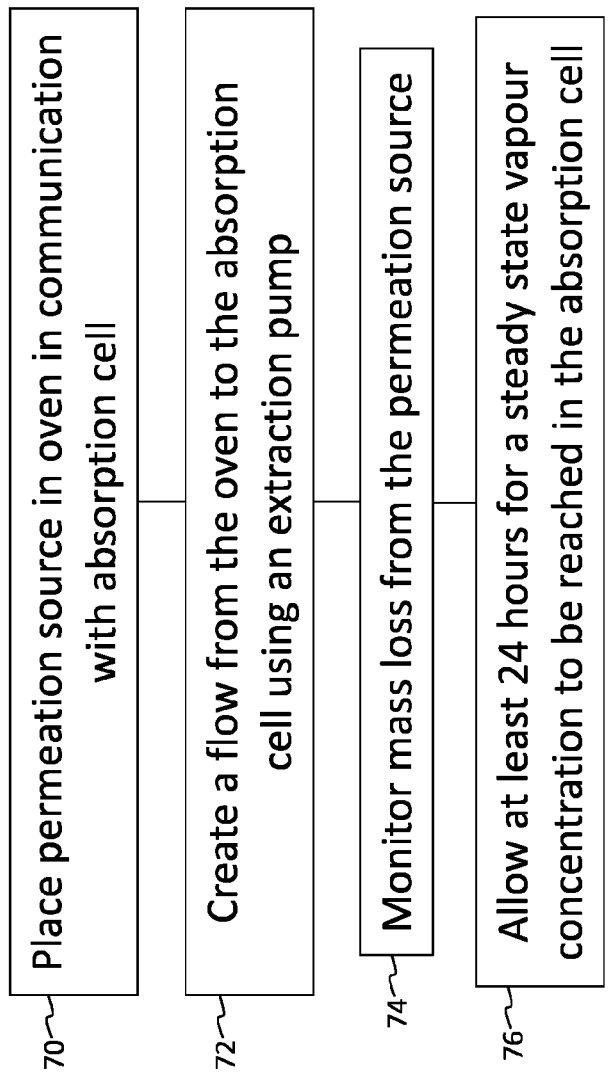
FIG. 6 is a flow chart further exemplifying the steps 22, 24 and 26 of the method of FIG. 2.

A controlled vaporisation of the sample compound is then carried out using the permeation tube 60. With reference to FIG. 6, the permeation tube 60 is placed at step 70 into the oven 6 which is in communication with the absorption cell 2 as shown in FIG. 1. The vapour is provided at low concentration in a carrier gas of pure nitrogen. A flow of the vapour and carrier gas is created at step 72 from the oven 6 to the absorption cell 2 using the extraction pump 12 and pressure controller 10. Oven temperature is controlled and the temperature inside the absorption cell 2 is monitored.

In order to obtain a quantitative spectrum, mass loss from the permeation source is monitored at step 74. A balance having an accuracy of at least 10 μg is used and a linear fit to mass loss data gives a permeation rate to an accuracy of 1%.

This gives a permeation rate that can be combined with the known flow rate through the cell 2 to calculate the concentration of vapour in the absorption cell 2 to a high degree of accuracy. For this calculation the following relation is used $$C = \frac{f}{F} \cdot \frac{RT}{MP}$$

where C is the concentration of the vapour phase sample, f is the permeation rate, F is the flow rate of gas through the cell 2, T is the temperature in the cell 2, P is the pressure in the cell 2, M is the molecular mass of the sample compound, and R is the ideal gas constant.

At least 24 hours, and optionally 2 days, are allowed for a steady state vapour concentration to be reached in the absorption cell 2.

With a steady state achieved at a known vapour concentration, the infrared absorption spectrum of the vapour is measured at step 28 with a multi-pass absorption system 80. As shown in FIG. 7, the system 80 comprises an absorption cell 2, transfer optics 82, and a vacuum adaptor 84 interfaced with a Fourier transform spectrometer 86. The absorption cell 2 has a stainless steel outer body that can be heated electrically by a surrounding jacket. The jacket helps to promote temperature homogeneity and to avoid condensation cold spots.

The absorption cell 2 is shown in more detail in FIGS. 8 and 9 with its outer body removed to show the optical arrangement. The absorption cell 2 has twin mirrors 90 at its cap and a single mirror 92 at its base in order to allow a beam to pass through the cell multiple times before exiting. The mirrors are gold coated and the optical input and output ports (for coupling the cell 2 to the transfer optics 82) are fitted with anti-reflection coated ZnSe windows.

Figure 10:
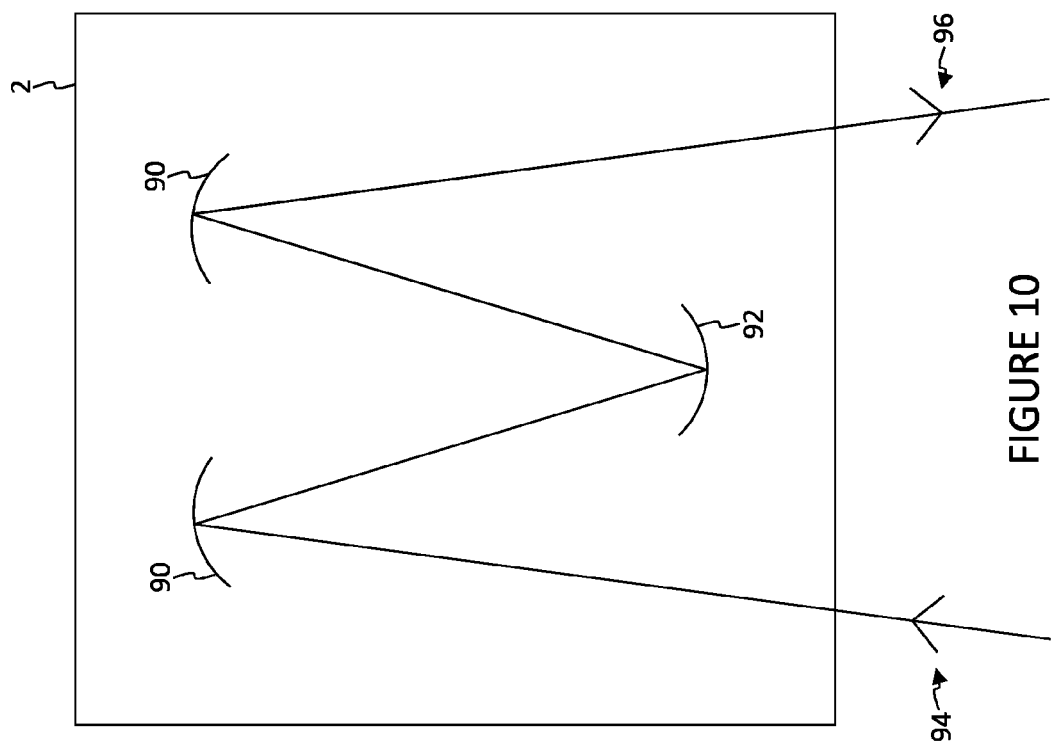
FIG. 10 is a schematic cross-sectional drawing of the beam path through the absorption cell of FIGS. 8 and 9.

An example of a multipass beam path is shown in FIG. 10: an input beam 94 enters the absorption cell and passes through vapour in the cell 2 before being reflected by one of the twin mirrors 90. The beam then passes back along the cell 2 before being reflected by the single mirror 92, before passing along the cell 2 again and being reflected by the other twin mirror 90. The beam then passes along the cell 2 a fourth and final time before exiting as exit beam 96. This well-known optical arrangement increases the effective path length through the absorption cell, thereby enabling a stronger absorption spectrum to be measured inside a limited volume. As is known, this approach can be extended to increase the number of times the beam passes along the cell 2 before exiting. The absorption cell 2 and transfer optics 82 are arranged to provide a path length of around 10 m.

As indicated above, the temperature inside the absorption cell 2 is monitored. This is done using a thermistor placed between the twin mirrors 90 so that the temperature of the steady state gas can be measured. This is preferable to measuring the temperature of actual components of the absorption cell 2 because the gas sample is only resident in the absorption cell for 4 minutes at a maximum flow rate and 40 minutes at a minimum flow rate, so thermal equilibrium between the gas and the absorption cell 2 may not have been established. Positioning the thermistor between the twin mirrors 90 provides a more reliable temperature measurement than positioning a thermistor near input and output ducts where the gas sample enters and leaves the cell 2.

Special considerations are required when isolating an explosive compound. Legal provisions regulate the safe transport of explosives and various explosives are commercially available for delivery in solution form. For safety, only small samples of explosives of the order of around 1 g are isolated from solution. Once isolated, the condensed phase samples require careful handling, in some cases avoiding sudden movements. Glassware of the rotary evaporator 30 is provided with an additional plastics coating in case of broken glass in the event of an explosion. A preferred solvent for explosives is dichloromethane, which has a relatively low boiling point of 40° C. As a result, a high vacuum within the rotary evaporator is not required and a water-aspirated pump is sufficient to create a partial vacuum within the evaporator, rather than a more powerful diaphragm pump. An evaporation flask 32 of volume 10 ml with a 10 mg/ml solution gives a maximum recovered mass of explosive of 100 mg, which is small enough to avoid an explosion. There is still a risk of deflagration (ie. rapid burning) but even in this event the glassware will not shatter.

For explosives dissolved in dichloromethane, the water bath of the rotary evaporator is set to 45° C., a few degrees above the solvent's boiling point. The required solution is handled with care during transfer from a storage fridge to the evaporator 30, and is transferred in a sealed and padded container. Once in the evaporation flask 32 and connected to the rotary evaporator 30 with the flask 32 just dipping into the water bath, a pressure of approximately 800 mBar is sufficient to evaporate the dichloromethane. Typical evaporation times are around 10 minutes.

This procedure to isolate the explosive compound from solution gives a purity of more than 99% of the isolated compound.

The isolated explosive is transferred from the evaporation flask 32 into a PTFE permeation tube 60 with an active length of 10 cm using a micro-spatula or a Pasteur pipette depending on whether the isolated condensed phase explosive is solid or liquid. Three 1.7 mm diameter holes are drilled into the tube membrane 62 to increase the permeation rate, and the tube 60 is sealed and placed in a plastic container for transport to the oven 6. The waste solvent is collected in a beaker and any spilt solvent is soaked onto tissue paper and burned in a fume cupboard. Glassware is cleaned with acetone and the solution of the explosive compound is returned to the storage fridge.

The pressure and temperature inside the absorption cell are set to and maintained at 760 Torr and 25.5° C. The gas line 8 is kept at a higher temperature to minimise condensation within the system. Mass loss data and spectra are then taken as described above.

In an alternative embodiment, mass loss data is not taken during the vaporisation experiment itself, but is rather taken during a pre-calibration of the permeation tube 60. In this approach, the permeation rate at a given temperature is already known when the experiment starts, so provided that the operating temperature is known, the permeation rate can be looked up.

Figure 11:
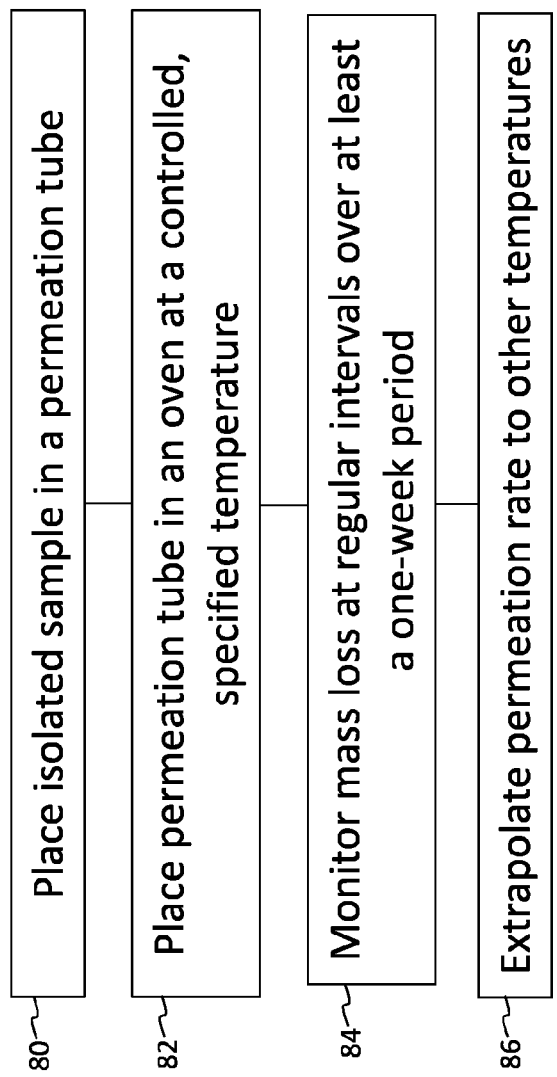
FIG. 11 is a flow chart showing a method of pre-calibrating a permeation tube according to a further embodiment of the invention.

In order to calibrate a permeation tube 60, a calibration process is followed to measure accurately the rate of mass loss of the sample from the permeation tube 60 at a known temperature. With reference to FIG. 11, an isolated sample of the compound is placed in a permeation tube 60 at step 80 and the tube 60 is placed at step 82 into an oven at a controlled, specified temperature. As indicated at step 84, mass loss is monitored at regular intervals over at least a one-week period, and optionally over two weeks or more. This time period provides an accurate calibration of the permeation tube 60 for the specified oven temperature. The measured permeation rate is then extrapolated at step 86 to other temperatures by calculation.

Whether mass loss is monitored in advance of or during the vaporisation experiment, the highest weighing accuracy is only possible under conditions of very high stability. Steps are taken to ensure high stability conditions. For example, the balance is placed on an actively damped, accurately levelled surface, and the environmental temperature is stabilised to within a few degrees. The balance control panel is detached from the balance and mounted independently of the damped surface so that user contact with the control panel does not result in mechanical disturbances of the balance itself. The sample to be measured is placed centrally on the balance. Gloves are worn by the user, air conditioning is switched on for at least four hours leading up to the calibration and then switched off for the calibration, when placed on the balance the permeation tube 60 is dusted off using compressed air and de-ionized for thirty seconds, and then mass loss data is taken.

The highest weighing accuracy under stable conditions gives a permeation rate to an accuracy of 1%. The measured permeation rate will be with respect to the operating temperature of the oven in which the permeation tube 2 was placed during the calibration process. The data can be extrapolated by post-analysis to give permeation rates for the tube 60 at other temperatures, but this post-calculation degrades the permeation rate accuracy to about 10%. In order to obtain permeation rates to an accuracy of 1% at more than one operating temperature, additional calibration is performed.

By way of example, the method of the invention may be used as follows to obtain a vapour phase spectrum of the explosive ethyl glycol dinitrate (EGDN).

Figure 12:
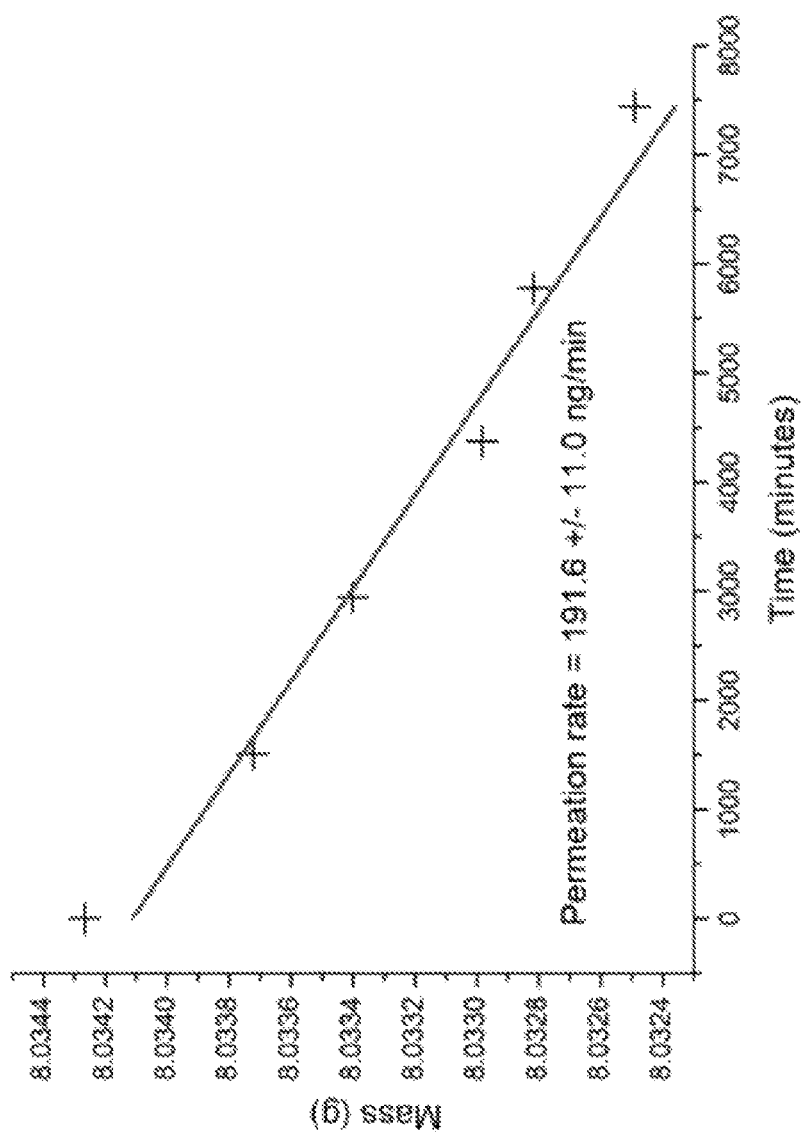
FIG. 12 is a graph obtained using the method of FIG. 2 showing mass loss over time of a permeation tube containing ethyl glycol dinitrate (EGDN)
Figure 13:
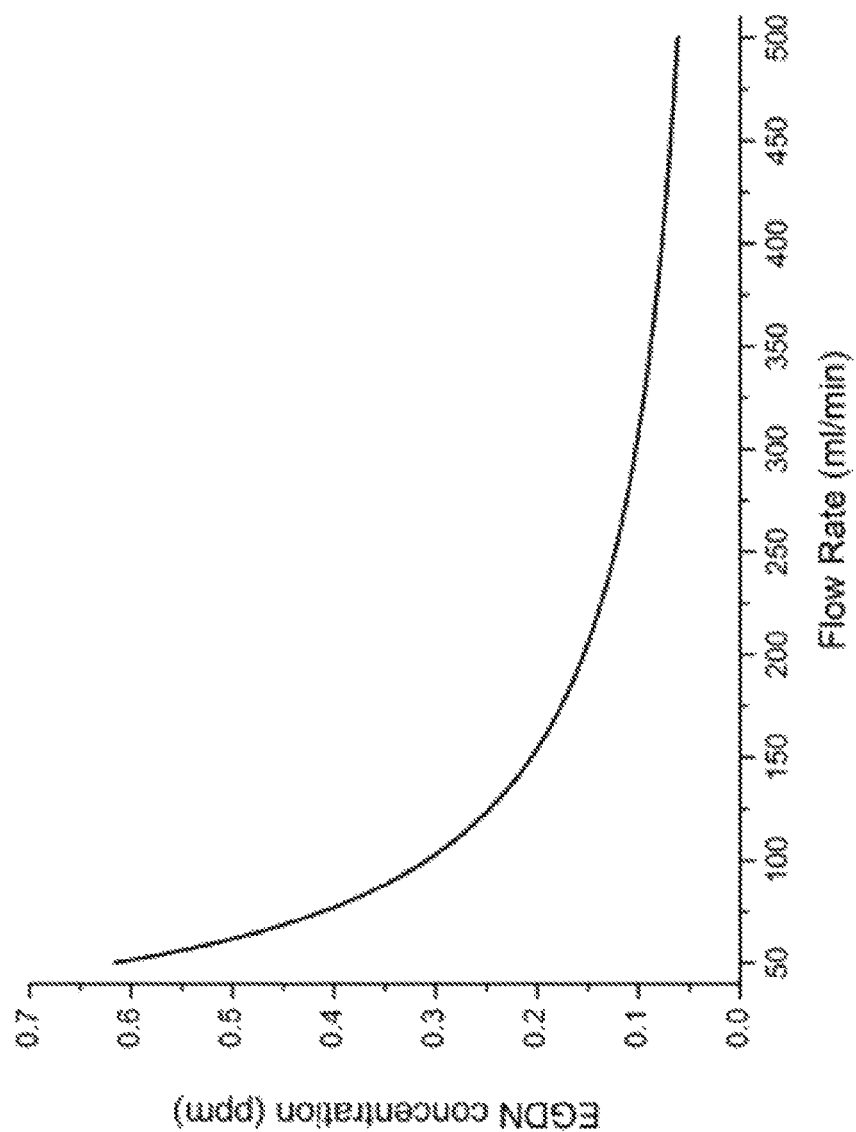
FIG. 13 is a graph obtained using the method of FIG. 2 showing EGDN vapour concentration in an absorption cell as a function of flow rate of gas flowing through the absorption cell.

A permeation source of EGDN is placed in an oven at a temperature of 30° C. Referring to FIG. 12, a linear fit to mass loss data gives a permeation rate of 191.6±11.0 ng/min with a 5.7% error, which gives a concentration of EGDN in the absorption cell 2 ranging from 61.6±4.7 ppbV at the maximum flow rate (500 ml/min) up to 616.6±47.7 ppbV at the minimum flow rate (50 ml/min). FIG. 13 shows calculated EGDN concentration in the absorption cell 2 as a function of flow rate. The permeation rate corresponds to a mass loss of 0.275 mg/day which limits the lifetime of the tube 60 to approximately 110 days assuming that 30 mg of EGDN was isolated from solution.

Figure 14:
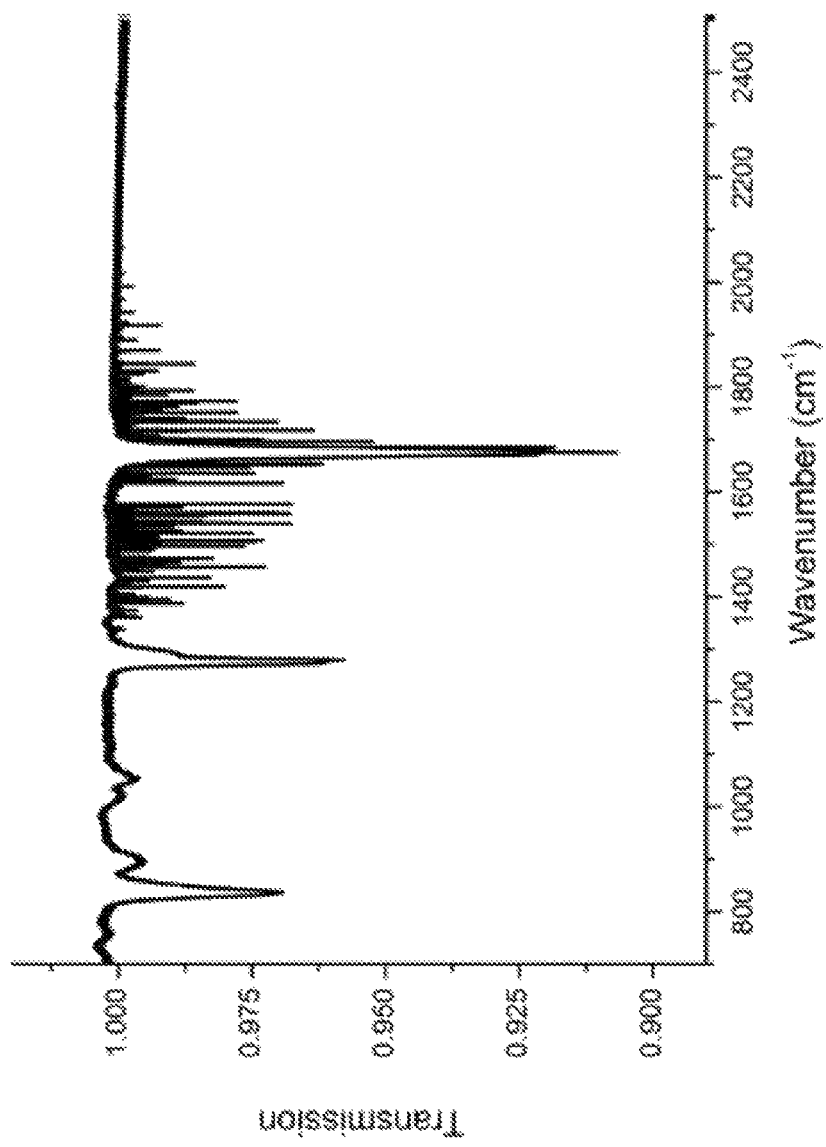
FIG. 14 is a graph obtained using the method of FIG. 2 showing a vapour phase transmission spectrum of EGDN.
Figure 15:
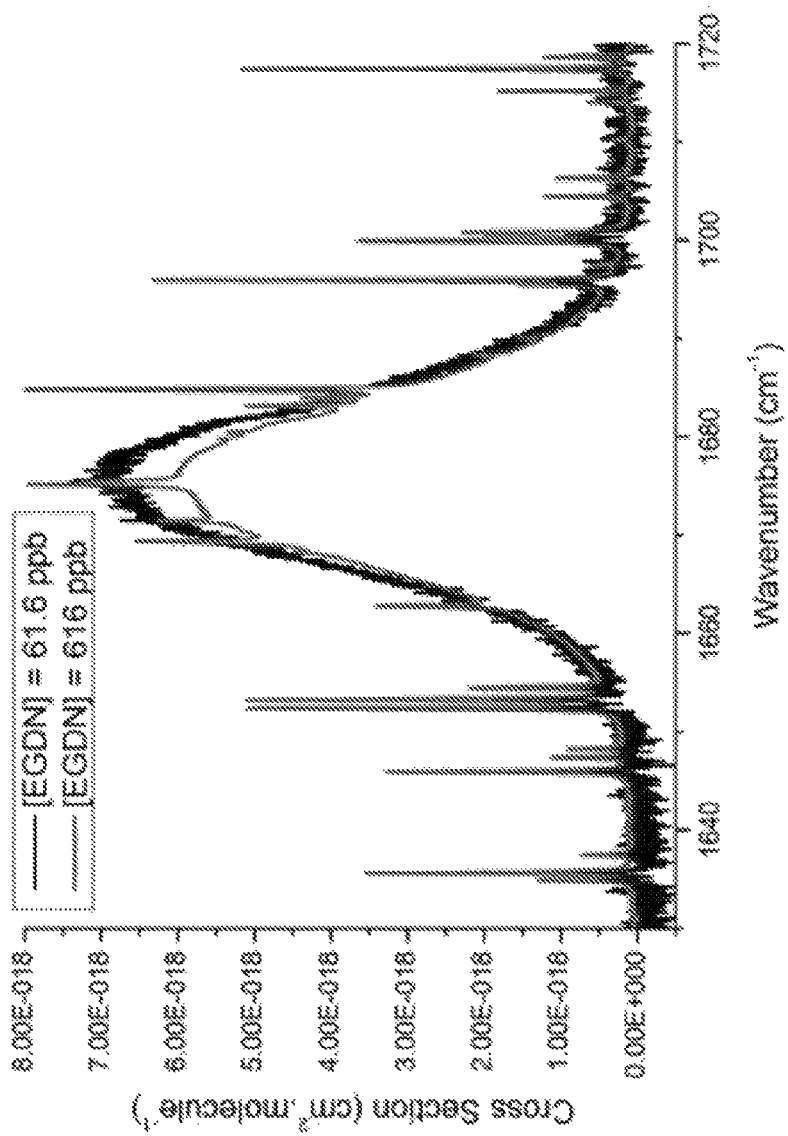
FIG. 15 is a graph obtained using the method of FIG. 2 showing vapour phase absorption spectra of EGDN at two different concentrations of EGDN.
Figure 16:
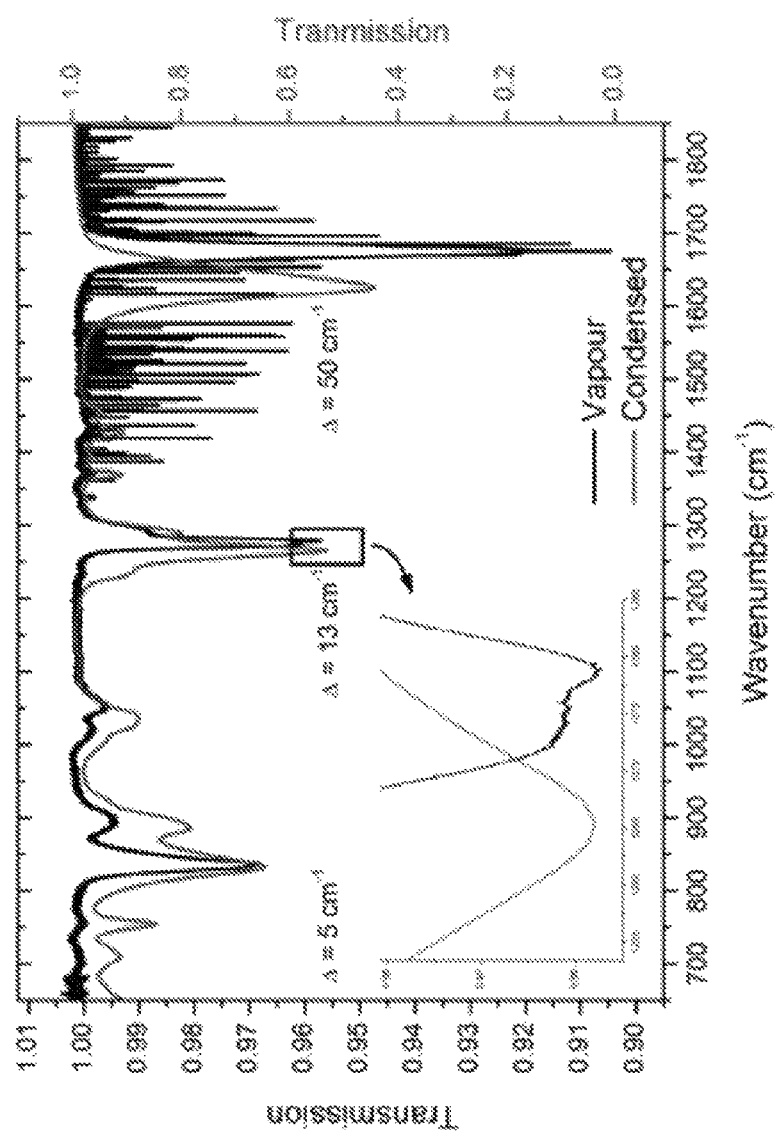
FIG. 16 is a graph obtained using the method of FIG. 2 showing vapour and condensed phase transmission spectra of EGDN, including an inset graph showing an enlarged version of a portion of the main graph of FIG. 16.

A transmission spectrum for EGDN obtained in this way is shown in FIG. 14, and an absorption spectrum for two different concentrations of the compound is shown in FIG. 15. In FIG. 16, aspects of the vapour and condensed phase transmission spectra of EGDN are compared.

Various differences are visible from the plot shown in FIG. 16 which differentiate the vapour phase and condensed phase spectra. Firstly, the band positions are displaced between the two spectra: for the three most intense bands, the band centre differences are 5 $cm^{-1}$ at 830 $cm^{-1}$, 13 $cm^{-1}$ at 1280 $cm^{-1}$, and 50 $cm^{-1}$ for the 1670 $cm^{-1}$ band. Secondly, the vapour phase bands are narrower than the liquid phase bands: for example, the 1670 $cm^{-1}$ vapour band has a linewidth (FWHM) of 24 $cm^{-1}$, while the equivalent liquid band has a linewidth of 44 $cm^{-1}$. Thirdly, the vapour phase bands exhibit some unique fine structure, as shown in the inset graph of FIG. 16.

As can be readily appreciated from the differences between the condensed phase and vapour phase spectra of EGDN, the unique features of a compound's vapour phase spectrum can be used to calibrate an optical instrument for detecting that compound in the vapour phase with an increased level of reliability.

Figure 17:
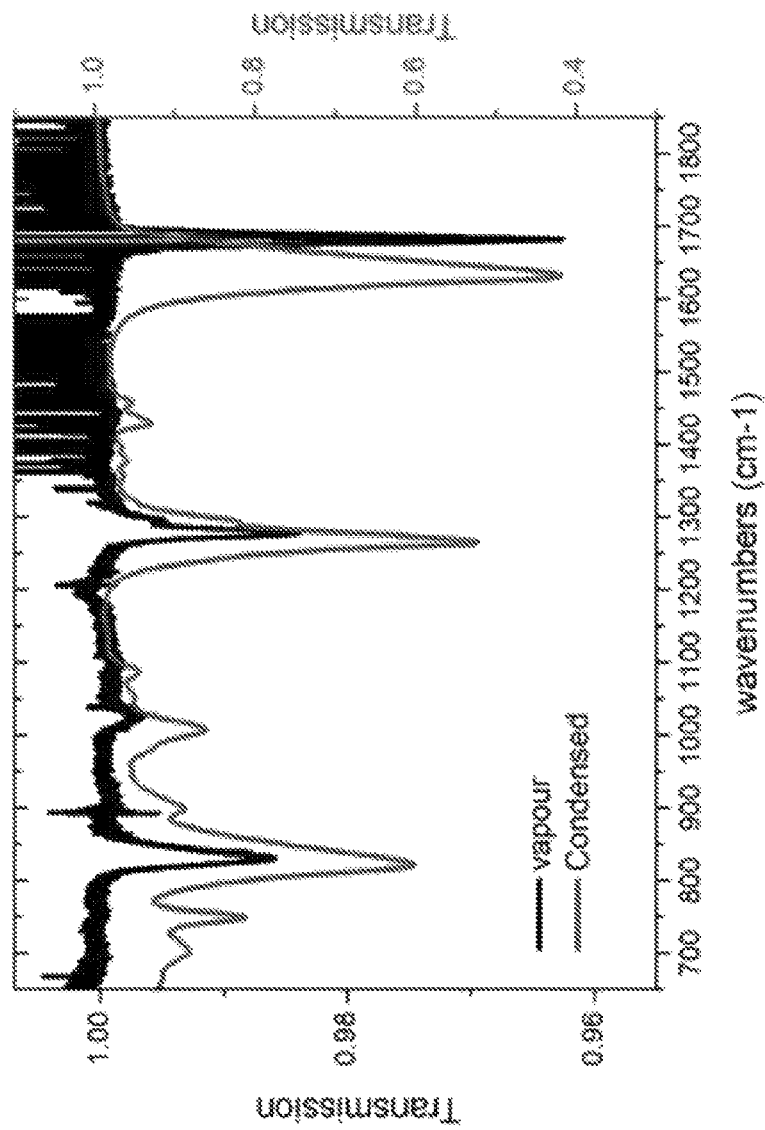
FIG. 17 is a graph obtained using the method of FIG. 2 showing vapour and condensed phase transmission spectra of nitroglycerin (NG)

By way of further example and with reference to FIG. 17, the method of the invention may be used to obtain a vapour phase spectrum of nitroglycerin (NG).

NG is sensitive to shock or static discharge and is therefore handled with particular care. As a safety measure during the isolation process, when the majority of solvent has been evaporated and the solution remaining in the evaporation flask 32 is highly concentrated NG, the rotation speed of the rotary evaporator 2 is reduced to avoid the formation of any bubbles whose collapse would risk igniting the NG. An NG mass loss rate from the permeation tube 60 of 83.0±1.0 ng/min with a 1.2% error is established with an oven temperature of 60° C. This results in NG vapour concentrations in the absorption cell 2 ranging from 17.9±0.6 ppb at a flow rate of 500 ml/min up to 178.8±5.7 ppb at a flow rate of 50 ml/min.

As can be appreciated, the concentrations of NG in the absorption cell 2 are lower than those indicated above for EGDN. This is because NG has a lower volatility, and as a result the absorption signals are weaker despite the higher oven temperature. Interfering signals from atmospheric molecules such as water vapour therefore become significant and post-processing of measured NG spectra is necessary to remove these effects.

As shown in the plot of FIG. 17, there are differences between the vapour phase and condensed phase spectra of NG that can enable an improved ability to reliably detect pure vapour phase NG.

Despite the lower volatility of NG and the associated lower absorption signals, an oven temperature of 60° C. for NG is reasonable because raising the temperature significantly, for example to 100° C., causes NG to dissociate into lighter molecules which interfere with the spectrum.

Figure 18:
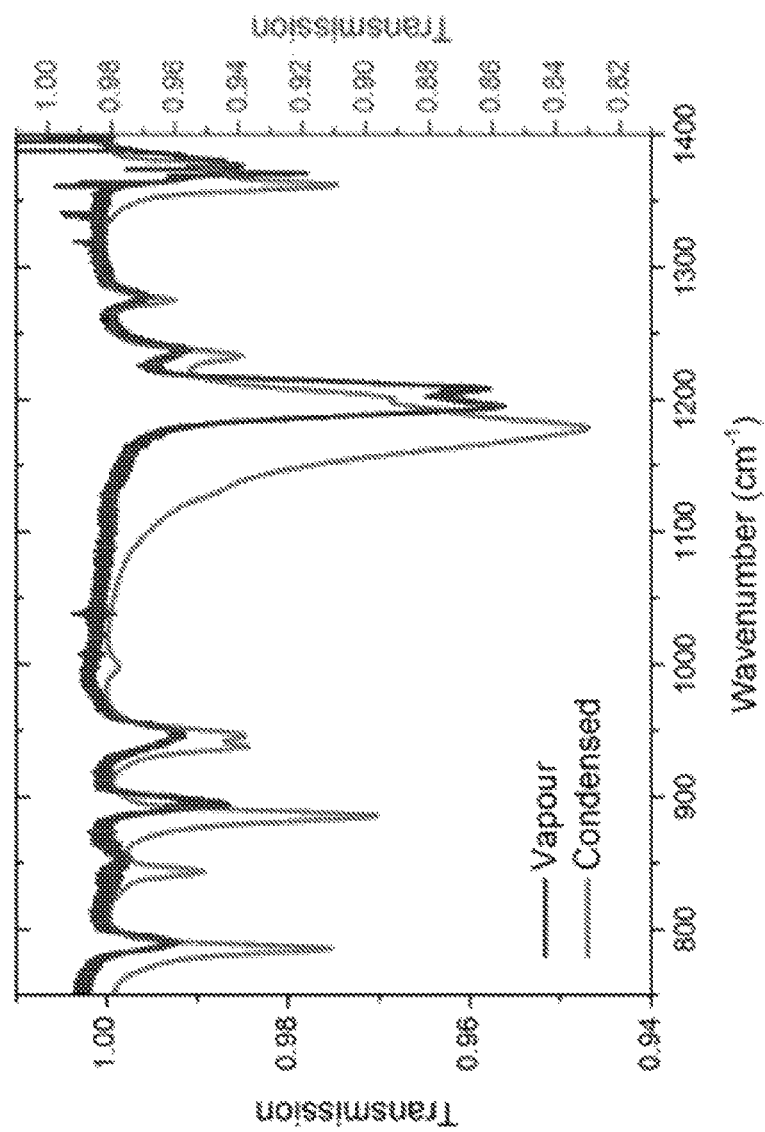
FIG. 18 is a graph obtained using the method of FIG. 2 showing vapour and condensed phase transmission spectra of triacetone triperoxide (TATP)

By way of further example and with reference to FIG. 18, the method of the invention may be used to obtain a vapour phase spectrum of triacetone triperoxide (TATP).

At an oven temperature of 40° C., small holes are drilled in the permeation tube membrane 62 in order to achieve a reasonable permeation rate of 208.1±2.7 ng/ml with a 1.3% relative error. This gives a TATP concentration in the absorption cell 2 ranging from 45.8 ppb at a flow of 500 ml/min up to 458 ppb at a flow of 50 ml/min.

As shown in the plot of FIG. 18, differences between the vapour phase and condensed phase spectra of TATP demonstrate the need for pure vapour phase reference spectra to reliably detect TATP in the vapour phase. Although not shown in FIG. 18, TATP also exhibits special spectral features in the vapour phase around 3000 $cm^{-1}$.

Figure 19:
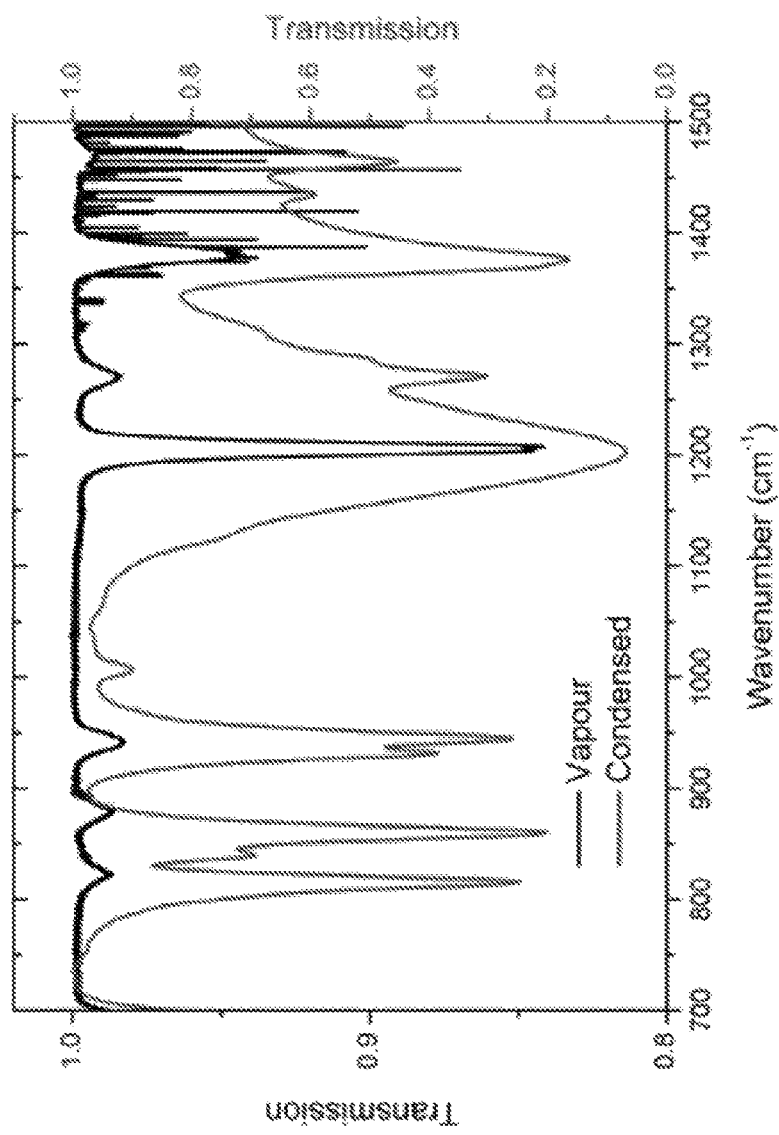
FIG. 19 is a graph obtained using the method of FIG. 2 showing vapour and condensed phase transmission spectra of diacetone diperoxide (DADP).

By way of further example and with reference to FIG. 19, the method of the invention may be used to obtain a vapour phase spectrum of diacetone diperoxide (DADP).

For DADP, an oven temperature of 40° C. is associated with a permeation rate of 764.9±12.1 ng/min with a 1.6% error. Concentrations of vapour phase DADP in the absorption cell 2 range from 253 ppb at a flow of 500 ml/min up to 2530 ppb at a flow of 50 ml/min. These concentrations of DADP are much higher than for TATP under similar conditions because of the higher volatility of DADP.

As shown in FIG. 19, the most intense bands for DADP in the vapour and condensed phases are very different. As a reference spectrum this offers improved detection of DADP in the vapour phase. DADP is a decomposition product of TATP, and any improvised explosive based on peroxides is likely to contain both TATP and DADP. The vapour phase spectra of TATP and DADP obtained using the method of the invention show sufficient differences to enable each species to be detected and quantified separately.

The invention claimed is:

1. A method of obtaining a quantitative vapour phase reference spectrum of a pure volatile compound, the method comprising the steps of:
providing an isolated pure condensed phase sample of the volatile compound;
vaporising the sample from a permeation source and supplying the vapour to an absorption cell of a spectrometer;
determining a rate at which vapour enters the absorption cell by measuring a rate of permeation from the permeation source by monitoring mass loss from the permeation source;
establishing and calculating a value of a steady state concentration of vapour in the absorption cell; and
measuring the spectrum of the vapour to determine a quantitative reference spectrum using the calculated vapour concentration.

2. A method according to claim 1, wherein the spectrum is an absorption spectrum.

3. A method according to claim 1, wherein the providing step comprises isolating the condensed phase sample by recovering it from a solution.

4. A method according to claim 1, wherein the isolated sample has a purity of at least 99% by mass.

5. A method according to claim 1, wherein the compound is an explosive.

6. A method according to claim 1, wherein the permeation source is provided in an oven at a controlled temperature to enable a controlled vaporisation of the compound from the permeation source.

7. A method according to claim 1, wherein mass loss is monitored using a balance having an accuracy of at least 10 µg.

8. A method according to claim 1, wherein the determining step comprises a pre-calibration step to pre-calibrate the permeation source.

9. A method according to claim 8, wherein the pre-calibration step comprises taking mass loss data in high stability conditions enabling measurement of a permeation rate to an accuracy of 1%.

10. A method according to claim 1, wherein measuring the mass loss is carried out during at least one of the establishing and measuring steps.

11. A method according to claim 1, wherein the establishing step comprises maintaining a steady flow through the absorption cell.

12. A method according to claim 1, wherein the steady state is established over a period of at least 24 hours.

13. A method according to claim 1, wherein the steady state concentration of the vapour is in the range 1 ppb to 3000 ppb.

14. A method according to claim 1, wherein the method further comprises monitoring the temperature in the absorption cell.

15. A method according to claim 1, wherein the spectrum is in the infrared.

16. A method according to claim 1, wherein the method further comprises comparing a measured vapour phase spectrum of the sample compound with a condensed phase spectrum of the same compound to identify distinguishing features for specific identification of the compound in the vapour phase.

17. A method according to claim 1, wherein the method further comprises using the spectrum to calibrate an optical instrument for detecting the compound in the vapour phase.

18. An instrument calibrated according to the method of claim 17.

19. An apparatus for obtaining a quantitative vapour phase reference spectrum of a pure volatile compound, the apparatus comprising:
- a vaporising chamber for receiving an isolated pure condensed phase sample of the volatile compound;
- a spectrometer including an absorption cell in fluid communication with the vaporising chamber;
- a monitoring device, including a device for monitoring mass loss from the isolated condensed phase sample, for monitoring the rate at which the compound in a vaporised form enters the absorption cell based on a rate at which the isolated condensed phase sample loses mass; and
- a flow drive for maintaining a steady flow of gas through the absorption cell in order to establish and calculate a value of a steady state concentration of the vaporised compound in the absorption cell ready for measurement of the vapour phase spectrum to determine a quantitative reference spectrum using the calculated vapour concentration.

* * * * *